United States Patent
Geise et al.

(10) Patent No.: US 7,008,394 B2
(45) Date of Patent: Mar. 7, 2006

(54) SYSTEM AND METHOD FOR PROCESSING BONE MARROW

(75) Inventors: Russell D. Geise, Allentown, PA (US); Robert J. Chapolini, Phoenix, MD (US)

(73) Assignee: BioAccess, Inc., Baltimore, MD (US)

( * ) Notice: Subject to any disclaimer, the term of this patent is extended or adjusted under 35 U.S.C. 154(b) by 0 days.

(21) Appl. No.: 10/240,168

(22) PCT Filed: Mar. 29, 2001

(86) PCT No.: PCT/US01/08625

§ 371 (c)(1),
(2), (4) Date: May 19, 2003

(87) PCT Pub. No.: WO01/72369

PCT Pub. Date: Oct. 4, 2001

(65) Prior Publication Data

US 2003/0208181 A1 Nov. 6, 2003

Related U.S. Application Data

(60) Provisional application No. 60/192,854, filed on Mar. 29, 2000.

(51) Int. Cl.
*A61M 37/00* (2006.01)
*A61B 19/00* (2006.01)

(52) U.S. Cl. ............. 604/6.15; 604/410; 600/575
(58) Field of Classification Search ............. 604/6.16, 604/522, 190, 257, 262, 317, 403, 406, 408, 604/409, 410; 210/767, 806, 348, 503; 128/DIG. 24; 424/140.1, 577; 435/2; 600/573, 575–580
See application file for complete search history.

(56) References Cited

U.S. PATENT DOCUMENTS

| | | | | |
|---|---|---|---|---|
| 4,481,946 A | * | 11/1984 | Altshuler et al. | 604/6.12 |
| 5,616,254 A | * | 4/1997 | Pall et al. | 210/806 |
| 5,724,988 A | * | 3/1998 | Dennehey et al. | 600/580 |

* cited by examiner

*Primary Examiner*—Nicholas D. Lucchesi
*Assistant Examiner*—Catherine S. Williams
(74) *Attorney, Agent, or Firm*—William J. Bundren (57) ABSTRACT

A system for collecting and processing donated bone marrow comprises a closed and/or sealable collection container and a closed and/or sealable satellite container. The system may also include at least one porous medium interposed between the collection container and the satellite container. The porous medium is a size gradient depletion media. The system may also include at least one third container in fluid communication with the collection container. The system may also include at least one manifold interposed in the fluid flow path between the collection container and the third container.

2 Claims, 2 Drawing Sheets

SYSTEM AND METHOD FOR PROCESSING BONE MARROW

TECHNICAL FIELD

This invention relates to a system for processing bone marrow donated for the purpose of therapeutic transfusion, for separating the bone marrow composition into one or more constituents, and, particularly, to improved methods and apparatuses for preparing and processing a bone marrow composition. This invention also relates to a biological fluid processing system for processing biological fluid into its various components.

BACKGROUND OF THE INVENTION

Bone marrow is a spongy tissue found inside bones. The bone marrow in the breast bone, skull, hips, ribs, and spine contains stem cells. Stem cells produce the body's blood cells, e.g., leukocytes, that fight infection); erythrocytes, that carry oxygen to and remove waste products from organs and tissues; and platelets, that enable the blood to clot.

Bone marrow, and some of the cells and cell types that are present in bone marrow, have been found to have significant therapeutic efficacy in the treatment of a number of diseases and conditions. For example, stem cells may be separated from the bone marrow composition and may be used in the treatment of many diseases. Filtered marrow itself may be used as a transplant graft in the treatment of leukemia, aplastic anemia, various lymphomas (e.g., Hodgkin's disease), multiple myeloma, certain immunodeficiencies, and a variety of cancers (typically solid tumors, such as breast and ovarian cancer).

The development of plastic blood collection bags has facilitated the separation of donated bone marrow into its various components and analogous products, thereby making these different components available as a transfusion product.

Further, significant improvements in reducing the immunogenicity of bone marrow transplanted into a patient has greatly increased the use of bone marrow as a competent and desirable therapeutic composition.

For these and other reasons, harvesting bone marrow and separating the bone marrow into components has substantial therapeutic and monetary value. This is nowhere more evident than in treating the increased damage to a patient's immune system caused by the higher doses and stronger drugs now used during chemotherapy for cancer patients. These more aggressive chemotherapy protocols are directly implicated in the reduction of the platelet content of the blood to abnormally low levels.

A conventional bone marrow collection procedure may include the following:

(1) Under general anesthesia, a bone marrow aspiration needle is inserted into the iliac crest (the cavity of the rear hip bone) where a large quantity of bone marrow is located. The bone marrow is extracted with a needle and syringe. Several skin punctures on each hip and multiple bone punctures are usually required to extract the requisite amount of bone marrow.

(2) About 10–30 cc of bone marrow are drawn from each bone puncture, and although the total amount drawn is variable (depending primarily on the size of the donor and the concentration of the bone marrow cells), usually about 1 liter and up to 1.5 liters of bone marrow are harvested.

(3) Each syringe of bone marrow drawn from the donor is then individually expressed into an open collection bag or an open container. The collection bag typically includes an anti-coagulant solution such as heparin and/or CPDA-1.

(4) The used syringe is then used to draw anti-coagulant solution into the syringe, the solution is expelled, and the syringe is used again to draw bone marrow. The process is repeated 30–50 times or more until up to about 1.5 liters of bone marrow is harvested.

(5) During or near the end of the collection process, a sample of about 5 cc is then drawn from the collection bag or container, and the amount of stem cells in the sample is either determined or inferred. Harvesting is usually completed when the sample contains about $1-3 \times 10^8$ nucleated cells per kilogram of body weight of the recipient.

(6) The harvested bone marrow composition is then filtered, generally within about 6 to 8 hours of harvesting. The filtration process usually involves a series of filters having different pore size ratings, typically $850\mu$, $500\mu$, and $200\mu$. These filters remove bone fragments, microaggregates, blood clots, and other undesirable debris from the bone marrow composition.

(7) The filtered bone marrow is then processed according to its end use. For example, if the bone marrow will be used in an autologous transplant, the filtered bone marrow will be frozen (cryopreserved) and stored at a temperature between about $-80°$ C. and about $-196°$ C. until the day of the transplant. For allogeneic transplants, the bone marrow will be treated to remove T-cells, then transferred directly to an infuser for administration to the patient.

The existing regimen for harvesting bone marrow is time-consuming and costly. Further, the present state of the art involves the use of open containers and/or open systems.

In view of this, there is a growing need for an efficient system and method for collecting and processing bone marrow, and for harvesting bone marrow in a closed or sealed system.

The devices and methods of this invention alleviate the above-described problems and, in addition, provide a higher yield of superior quality bone marrow.

A problem attendant with the separation of various blood and bone marrow components using a multiple bag system is that the highly valuable components become trapped in the conduits connecting the various bags and in the various devices that may be used in the system. Conventional processing and storage techniques contribute to these problems. For example, air, in particular oxygen, present in stored blood and blood components, or in the storage container, may lead to an impairment of the quality of the blood components, and may decrease their storage life. More particularly, oxygen may be associated with an increased metabolic rate (during glycolysis), which may lead to decreased storage life, and decreased viability and function of whole blood cells. For example, during storage red blood cells metabolize glucose, producing lactic and pyruvic acids. These acids decrease the pH of the medium, which in turn decreases metabolic functions. Furthermore, the presence of air or gas in the satellite bag may present a risk when a patient is transfused. For example, as little as 5 ml of air or gas may cause severe injury or death. Despite the deleterious effect of oxygen on storage life and the quality of bone marrow blood and bone marrow components, the prior art has not addressed the need to remove gases from bone marrow processing systems during collection and processing.

Because of the high cost and limited availability of bone marrow components, a device comprising a porous medium used to deplete leucocytes from biological fluid should deliver the highest possible proportion of the component present in the donated bone marrow. An ideal device for the filtering or leucocyte depletion of bone marrow would be inexpensive, relatively small, and be capable of rapidly processing the components obtained from about one unit or more of biological fluid (e.g., donated bone marrow), in, for example, less than about one hour. Ideally, this device would reduce the leucocyte content to the lowest possible level, while maximizing the yield of a valuable blood component while minimizing an expensive, sophisticated, labor intensive effort by the operator of the system. The yield of the bone marrow or a component should be maximized while at the same time delivering a viable and physiologically active component. It may also be preferable that the bone marrow filter or porous medium be capable of removing platelets, as well as fibrinogen, fibrin strands, tiny fat globules, and other components such as microaggregates which may be present in the bone marrow.

Definitions

The following definitions are used in reference to the invention:

(A) Bone marrow or Biological Fluid is the soft tissue within bone cavities, and typically contains whole blood, hematopoietic precursor cells and hematopoietic cells that are maturing into erythrocytes, five types of leukocytes, and thrombocytes. Harvested bone marrow typically includes these components, as well as bone chips, megakaryocytes, stem cells, fat globules, blood clots, fibrin, platelets, among other biological and/or cellular matter. Bone marrow or biological fluid also includes any treated or untreated fluid associated with living organisms, particularly bone marrow, including harvested unseparated (whole) bone marrow, warm or cold bone marrow, cryopreserved bone marrow, and stored or fresh bone marrow, treated bone marrow, such as bone marrow diluted with a physiological solution, including but not limited to saline, nutrient, and/or anticoagulant solutions; one or more bone marrow components, such as stem cells; and analogous bone marrow products derived from bone marrow or a bone marrow component. The biological fluid may include leucocytes, or may be treated to remove leucocytes. As used herein, bone marrow product or biological fluid refers to the components described above, and to similar bone marrow products or biological fluids obtained by other means and with similar properties. In accordance with the invention, each of these bone marrow products or biological fluids is processed in the manner described herein.

A typical harvesting procedure commonly draws up to about 1.5 liters of a composition containing bone marrow from the donor into a bag which contains an anticoagulant to prevent the bone marrow from clotting. However, the amount drawn differs from patient to patient and donation to donation.

(B) Filtered bone marrow: refers to a composition containing bone marrow and stem cells that is suitable for use as a transplant graft or an organ graft. The bone marrow harvested from a donor is treated and processed using various regimens before it is suitable for use as a transplant graft. For example, the harvested bone marrow may be mixed with a nutrient and/or anti-coagulant solution, and may be filtered to remove debris and the like.

(C) Porous medium: refers to the porous medium through which one or more bone marrow, bone marrow components, or biological fluids pass. A typical porous medium is a filter for removing undesirable constituents, such as pieces of bone, microaggregates, blood clots, and the like, from the bone marrow. The bone marrow processing system may optionally include a leucocyte depletion filter or porous medium, which refers generically to any one of the media which deplete leucocytes from the bone marrow or a bone marrow component.

The porous media according to the invention may be connected to a conduit interposed between the containers, and may be positioned in a housing which in turn can be connected to the conduit. As used herein, filter assembly refers to the porous medium positioned in a suitable housing. An exemplary filter assembly may include pore size filter assembly and/or a leucocyte depletion assembly or device. A biological fluid processing system, such as a bone marrow collection and processing system, may comprise porous media, preferably as filter assemblies.

SUMMARY OF THE INVENTION

In the devices and methods of the present invention, bone marrow is harvested from a donor and collected or pooled in a collection bag. Typically, the bone marrow is filtered at the time of processing, which, in the United States, is generally within about 6 to 8 hours of the time the bone marrow is harvested. Thus, as a biological fluid is transferred from the collection bag, debris and other undesirable constituents may be removed by the appropriate porous medium, and filtered bone marrow is collected in the satellite bag.

In accordance with the invention, a system is provided whereby a biological fluid such as bone marrow or a bone marrow composition is processed to form a bone marrow composition suitable for transplantation into a recipient, or is processed into one or more of its components. An apparatus and system according to the invention includes a closed collection container having at least one access port and a first connector for communicating with a second, transfer, or satellite container; and a transfer or satellite bag configured to establish fluid flow between the first container and the second container.

Some embodiments of the invention also include at least one filter assembly interposed in the fluid flow path between the first container and the second container. The filter assembly may be configured to establish and receive fluid flow from the collection container, said filter assembly having at least one porous medium through which bone marrow passes, said filter assembly may also be configured to establish fluid flow into a transfer or satellite bag.

Some embodiments of the invention also include at least one third container, preferably in fluid communication with the first container. Typically, the third container will include an anti-coagulant solution, a nutrient solution, a rinsing solution, a priming solution, or the like.

Some embodiments of the invention also include at least one manifold interposed between the first container and the second container. The manifold may be configured to establish a fluid flow path into the first container, into the third container, and/or between the first container and the second container.

for transferring the harvested bone marrow from the syringe to the collection bag. In preferred embodiments of the invention, the manifold includes one or more ports for transferring bone marrow, harvested from the donor in a harvesting container (typically a syringe), into the first or collection container.

Additionally, processes and systems according to the invention may include a gas outlet that allows gas that may be present in the system out of the system or a component of the system.

Processes and systems according to the invention may also include a gas inlet that allows gas into the system to recover a biological fluid that may be entrapped or retained during processing.

SPECIFIC DESCRIPTION OF THE INVENTION

The present invention involves a bone marrow collection and processing assembly or system comprising a closed or sealed first container and a closed or sealed second container, and a conduit interconnecting the first container with the second container, said first container having at least one access port.

Some embodiments of the invention also include at least one first porous medium interposed in the fluid flow path between the first container and the second container. The porous medium, preferably housed in a chamber to form a filter assembly, may include a microaggregate filter element and/or a gel pre-filter element. In a preferred embodiment of the invention, the system includes at least one microaggregate filter having a pre-determined pore size; in a most preferred embodiment of the invention, the system includes at least one microaggregate filter having a pore size selected from 850μ, 500μ, and 200μ, or combinations thereof.

Some embodiments of the invention also include at least one third container in fluid communication with the first container. Typically, the third container will include an anti-coagulant solution, a nutrient solution, a rinsing solution, a priming solution, or the like. It is intended that the invention should not be limited by the type or use of solution in the third container.

Some embodiments of the invention also include at least one manifold interposed in the fluid flow path between the first container and the third container. The manifold may be variously configured and multi-functional. For example, the manifold may include at least one port adapted to engage a portion of the harvesting container, said port being configured to establish a fluid flow path between the harvesting container and the first container. The port may also be configured to establish a fluid flow path between the harvesting container and the third container. For example, it may be desirable to transfer a bone marrow composition in a syringe (e.g., a harvesting container) to the first container or a collection container, and for drawing and expressing anti-coagulant solution into and out of the syringe.

In the embodiments of the invention that include a manifold, the manifold may be variously configured. In accordance with the present invention, the manifold may be configured or adapted to provide one or more of the following: a fluid flow path between the harvesting container and the collection container, a fluid flow path between the harvesting container and a third container, a fluid flow path between the third container and the collection container, or combination thereof. In a preferred embodiment of the invention, the manifold is configured to provide a individual fluid flow paths between the harvesting container, the collection container, and the third container.

A system according to the invention also includes one or more flow restrictors so that the collection container, the filter assembly, the transfer container, the third container, the manifold, or combinations thereof may be separated from the system.

The bone marrow collection and processing system may also include one or more fluid flow valves for opening and/or closing a fluid flow path anywhere in the system, or for channeling fluid through a specific fluid flow path. Exemplary fluid flow valves include but are not limited to a stopcock, a plunge valve, and a re-sealable septum valve. The fluid flow valves may by unidirectional or multi-directional. In some of the fluid flow valves, it may be desirable that the valve is re-sealable or closable.

As shown in more detail below, the assembly may also include additional containers, porous media, and conduits interconnecting the various elements of the system or assembly.

The invention also involves a method for collecting and processing bone marrow comprising harvesting bone marrow from a donor, collecting the bone marrow in a first closed or sealed container; passing the bone marrow through at least one porous medium, the porous medium comprising a microaggregate filter having a pre-determined pore size or rating; and passing the filtered bone marrow into a second closed or sealed container. In a preferred embodiment of the invention, the porous medium is positioned in a housing to form a filter assembly, and the filter assembly is interposed in the fluid flow path between the first container and the second container. In a most preferred embodiment of the invention, multiple filter assemblies are interposed in the fluid flow path between the first container and the second container, each filter assembly having a porous medium of different pore rating than the other porous media. In general, harvested bone marrow is processed or filtered as soon as practicable after donation in order to more effectively reduce or eliminate contaminating factors, including but not limited to leucocytes and microaggregates.

The invention also involves a method for collecting and processing bone marrow comprising harvesting bone marrow from a donor into a harvesting container, such as a syringe or the like; transferring the harvested bone marrow into a closed or sealable collection container; repeating the harvesting step and the transferring step until a sufficient quantity of bone marrow and/or stem cells are obtained, and collecting the bone marrow in the collection container. The method may further include passing the harvested bone marrow in the first container through a first porous medium, the first porous medium comprising a microaggregate filter having a pre-determined pore size or rating; and passing the filtered bone marrow into a second closed or sealable container.

In a preferred embodiment of the invention, transferring the harvested bone marrow into a collection container may include passing the bone marrow through a first fluid flow path into the collection container, closing the first flow path, opening a second fluid flow path between a third container containing anti-coagulant solution and the harvesting container; passing anti-coagulant solution into the harvesting container; expressing anti-coagulant solution from the harvesting container, preferably into the third container; closing the second flow path; and repeating the harvesting step and the transferring step until a sufficient quantity of bone marrow and/or stem cells are obtained.

In a most preferred embodiment of the invention, the transferring step includes repeating the harvesting step and the transferring step until a sufficient quantity of bone marrow and/or stem cells are obtained, then opening a fluid flow path between the first container and the third container, and expressing the contents of the third container into the first container.

In a preferred embodiment of the invention, the bone marrow collection and processing system is sealed and/or closed.

Figure 1:
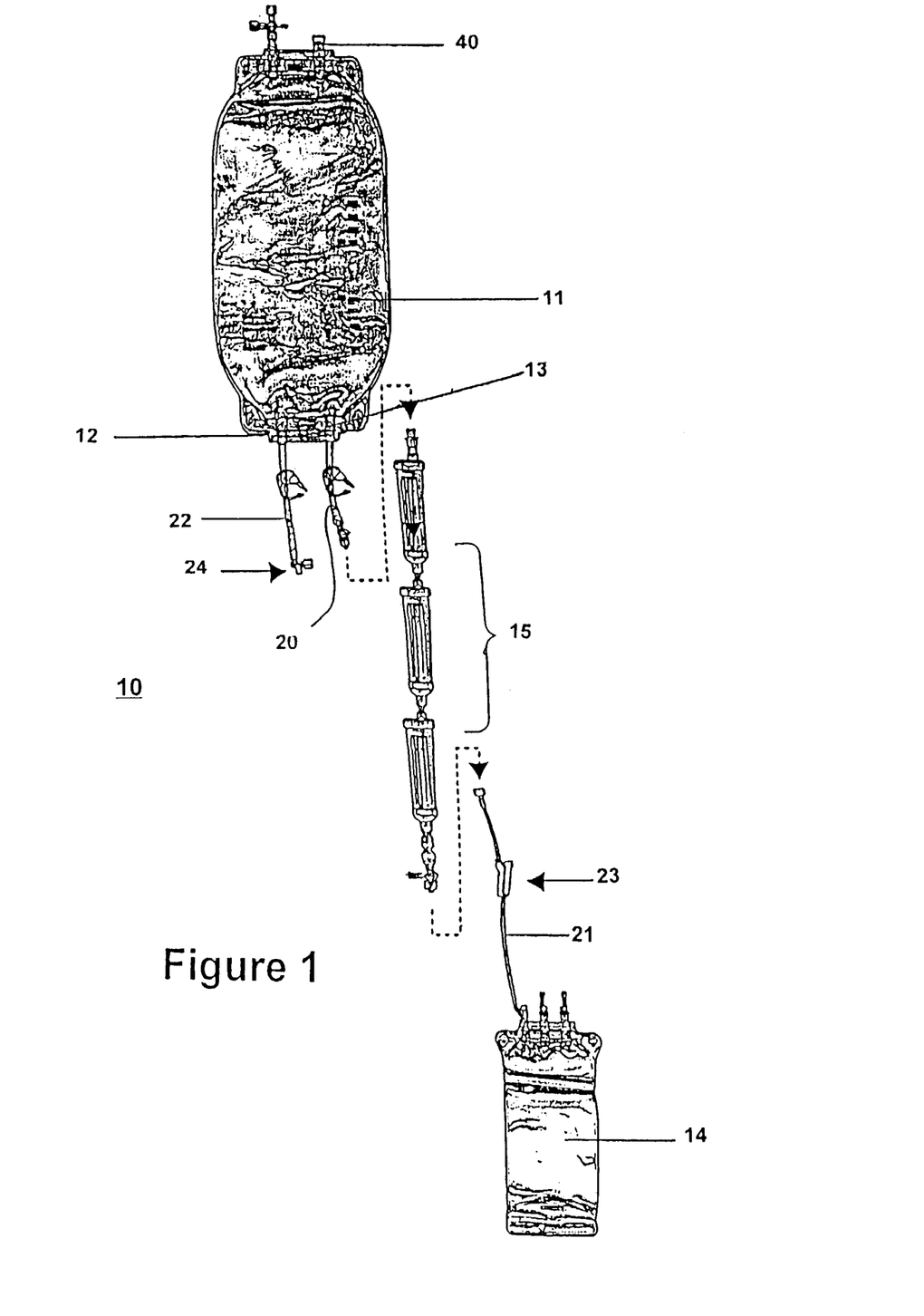
FIG. 1 is an embodiment of a biological fluid processing system according to the invention.

An exemplary bone marrow or biological fluid collection and processing system is shown in FIG. 1. The bone marrow processing system is generally denoted as 10. It may comprise a first container or collection bag 11, said first container comprising at least one access port 12 and at least one discharge port 13; a second container (first satellite bag) 14; and, interposed between the first container 11 and the second container 14, at least one filter assembly 15. Each of the assemblies or containers may be in fluid communication through tubing, preferably flexible tubing, 20, 21, and 22. In accordance with the invention, there is a first fluid flow path between the first container 11 and second container 14. A seal, valve, clamp 23, or transfer leg closure or cannula (not illustrated) may also be positioned in or on the tubing or in the collection and/or satellite bags. The seal (or seals) is opened when fluid is to be transferred between bags.

In a preferred embodiment of the invention, first container 11 also includes at least one valve 24, preferably in fluid communication with access port 12. In the illustrated embodiment, valve 24 is in fluid communication with port 12 through conduit 22. Valve 24 permits access to the collection bag; in a preferred embodiment of the invention, valve 24 is or includes a connector adapted for communication with a syringe or the like, e.g., a Luer lock.

An apparatus or system according to the invention may also include one or more manifolds 30. Manifold 30 may be variously configured to provide closed and/or sealed fluid communication between a harvesting container (not shown) and first or collection container 11, to provide closed and/or sealed fluid communication between a harvesting container (not shown) and third container 34, to provide closed and/or sealed fluid communication between first container 11 and third container 34, to provide fluid communication between first container 11 and a sampling container (not shown), such as a syringe, or combinations thereof. An embodiment of the invention is illustrated in FIG. 2.

Figure 2:
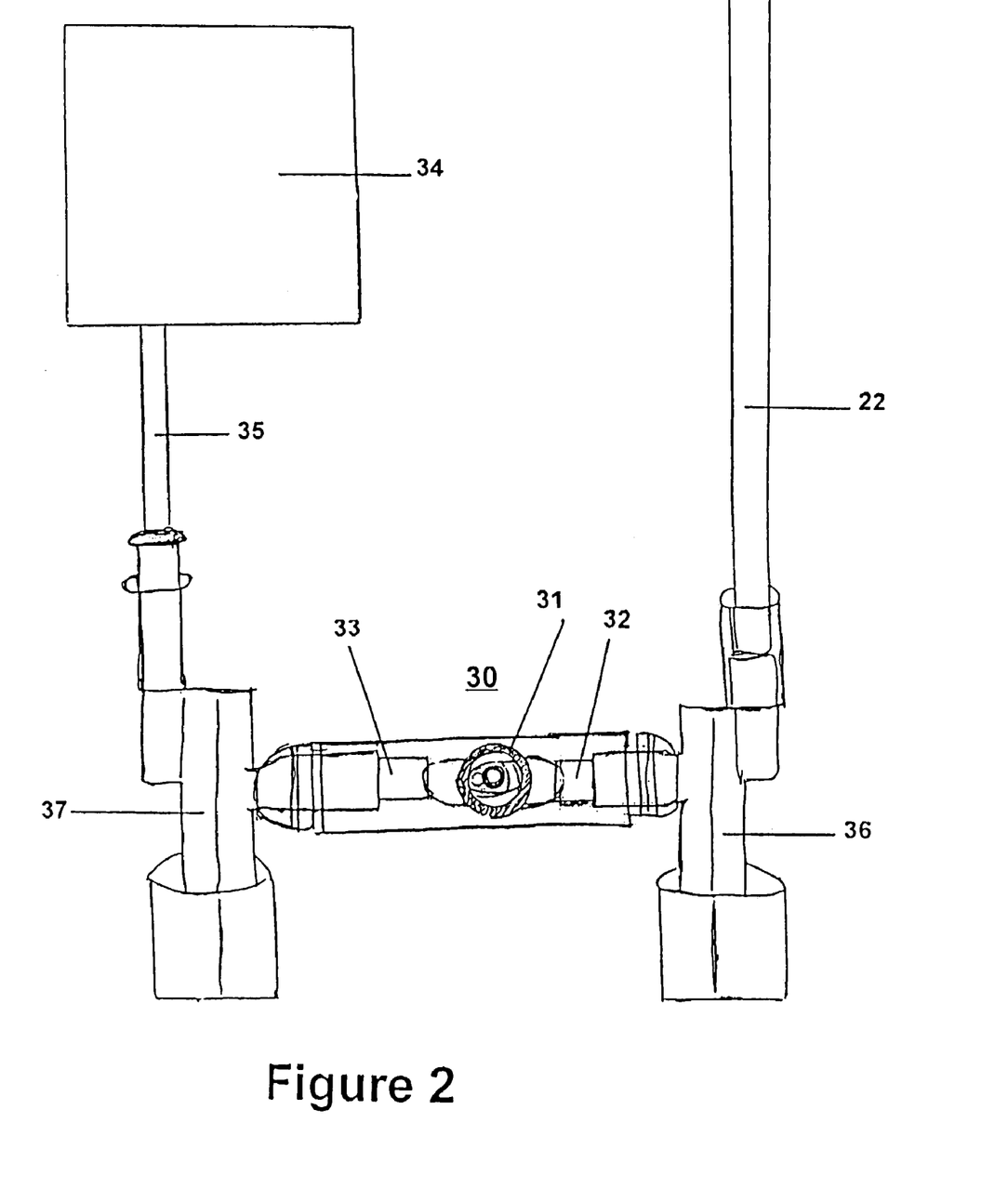
FIG. 2 is an embodiment of a manifold for transferring bone marrow into a processing system according to the invention.

In FIG. 2, manifold 30 is in fluid communication with first container 11 through conduit 22. Manifold 30 includes port 31 configured to engage complementary structures on a harvesting container (e.g., a syringe, not shown). In a preferred embodiment of the invention, the harvesting container includes a connector or the like suitable for engaging port 31. Such connectors are well known in the art, and include but are not limited to a Luer lock.

Manifold 30 may include a channel, conduit 32, or the like, that defines a fluid flow path between the harvesting container and the collection container. Manifold 30 may include a channel, conduit 33, or the like, that defines a fluid flow path between the harvesting container and a third container 34. Third container 34 preferably contains an anti-coagulant solution, such as heparin, CPDA-1, DMSO, or the like. Third container 34 may be directly attached to the manifold, may itself include structures that function as a manifold as defined herein, or may be connected to the manifold 30 through conduit 35. Manifold 30 may include a channel, conduits 32 and 33, or the like, that defines a fluid flow path between the first container 11 and the third container 34.

In a system according to the invention, the flow path between the first container and the harvesting container is the second fluid flow path; between the harvesting container and the third container, the third fluid flow path; and between the first container and the third container, the fourth fluid flow path.

In a preferred embodiment of the invention, the second, third and/or fourth fluid flow paths may include one or more valves, preferably in fluid communication with access port 31. The valves may be an element integral to a container or manifold, or may be connected to a container or manifold. In the illustrated embodiment, valve 36 is interposed in the fluid flow path between first container 11 and manifold 30, and valve 37 is interposed in the fluid flow path between third container 34 and manifold 30. In accordance with the invention, valves 36 and 37 may be any valve, clamp, restrictor, diaphragm, connector, or the like that selectively permits fluid flow therethrough, and is suitable for use with a composition containing bone marrow and/or anti-coagulant solution. In a preferred embodiment of the invention, valves 36 and 37 are plunge valves, valves that open a channel when the plunger is depressed. Suitable valves are commercially available under the tradename TRAC™ Valve.

As noted above, a system according to the invention also preferably includes one or more sampling ports. For example, ports 12, 13, and 31 may function as sampling ports. In a preferred embodiment of the invention, first container 11 includes sampling port 40. In a most preferred embodiment of the invention, the sampling port maintains the assembly or system in a closed and/or sealed condition. For example, sampling port 40 may include a re-sealable septum or diaphragm or the like that permits the insertion of a needle into the first container, and re-seals the first container when the needle is withdrawn.

One skilled in the art will recognize that multiple harvesting containers and/or multiple manifolds may be incorporated into a system according to the invention.

In accordance with the present invention, any number and combinations of assemblies, porous media, containers, conduits, and methods of operation or processing are suitable. The invention comprises structures and methods for harvesting a composition comprising bone marrow, transferring the harvested bone marrow to a collection container, and processing the collected bone marrow, more preferably into a composition containing bone marrow suitable for use as a transplant graft. One skilled in the art will recognize that the invention as described here may be reconfigured into different combinations, elements, and processes which are included within the scope of the invention.

A method according to the present invention includes harvesting a composition comprising bone marrow, passing the bone marrow through a system according to the present invention, and processing the bone marrow into a composition suitable for a pre-determined end use, e.g., suitable as a transplant graft, as a source of stem cells, or as a composition suitable for use as part of research and development related to one or more constituents in the bone marrow composition. As will be readily apparent to one skilled in the art, methods, steps, or a specific sequence of steps according to the invention will be dictated in part by the specific elements incorporated in a specific system. For example, methods relating to a system lacking a third container would not include steps that involve the third container.

The following provides exemplary methods and specific exemplary steps to illustrate the function of an apparatus and system according to the present invention.

Once a donor is prepared for a bone marrow harvest procedure, bone marrow from the donor may be drawn into a harvesting container, such as a syringe. Typically, about 5 cc to about 30 cc of bone marrow are drawn. The harvesting container is then disconnected from the donor and attached to an apparatus according to the present invention. For example, a harvesting syringe may be connected to access port 12 on first or collection container 11 or on access port 31 on manifold 30. Collection container 11 typically includes a pre-determined amount of anti-coagulant solution, and the harvested bone marrow is mixed with the anti-coagulant solution. In use, a biological fluid, e.g., bone marrow, is fed under sufficient pressure into the inlet of container 11 from any suitable source of the biological fluid. For example, bone marrow may be harvested from a donor using a syringe or the like, and the bone marrow may be injected from a syringe into the inlet of the collection container 11.

In the embodiments of the invention that include a manifold 30, the harvested bone marrow may be expressed or passed from the harvesting container through port 31, through open valve 36, through conduit 22, and into collection bag 11. Valve 36 is then closed, valve 37 is then opened, and anti-coagulant solution in third container 34 may be expressed or drawn into the harvesting container through conduit 35, valve 37 conduit 33, and port 31. Once the harvesting container is flushed or rinsed with anti-coagulant solution, the solution may be returned to third container 34, and the harvesting container is ready for re-use, i.e., for drawing another 5–30 cc of bone marrow from the patient.

The harvesting step and the transfer of the bone marrow composition to the collection container may be repeated as often as desired, typically until up to about 1.5 liters or more of bone marrow is harvested.

Once the desired amount of bone marrow is harvested, if the system includes a third container 34, the contents of third container 34 (typically including a mixture of anti-coagulant solution and bone marrow rinsed from the harvesting container), may be expressed or passed into first container 11, where it is mixed with the bone marrow composition collected in first container 11. In the embodiment of the invention shown in FIGS. 1 and 2, a fluid flow path is opened between third container 34 and first container 11, typically by opening valve 37, closing port 31, opening valve 36, and opening port 12. The composition in first container 11 at this point in the process is referred to as the collected bone marrow composition.

At this point in the method, or earlier, it may be desirable to test or sample the composition in the first container 11. In this embodiment of the invention, a sampling device (not illustrated) may be inserted through re-sealable sampling port 40 and into the composition contained therein. Once a sample is withdrawn from the container, sampling port 40 preferably closes or re-seals.

The collected bone marrow may then be processed by opening or establishing fluid communication between the first container 11 and the second container 14. By creating a pressure differential between first container 11 and second container 14, biological fluid will flow from the first container to the second container. In accordance with some embodiments of the invention, the bone marrow will be filtered as desired if a filter assembly is interposed in the fluid flow path between the first container 11 and the second container 14.

The invention also involves a method for harvesting, collecting, and processing bone marrow comprising harvesting bone marrow in a container, collecting bone marrow in a collection container; and passing the bone marrow through a filter assembly and into a second container.

In general, donated bone marrow is processed as soon as practicable in order to more effectively reduce or eliminate contaminating factors, including but not limited to leucocytes and microaggregates.

Each of the components of the assembly will now be described in more detail below.

The containers which are used in the biological fluid processing assembly may be constructed of any material compatible with a biological fluid, such as bone marrow or a bone marrow component, and is capable of withstanding a sterilization environment. A wide variety of these containers are already known in the art. For example, bone marrow collection and satellite bags are typically made from plasticized polyvinyl chloride, e.g. PVC plasticized with dioctylphthalate, diethylhexylphthalate, or trioctyltrimellitate. The bags may also be formed from polyolefin, polyurethane, polyester, and polycarbonate.

As used herein, the tubing may be any conduit or means which provides fluid communication between the containers, and is typically made from the same flexible material as is used for the containers, preferably plasticized PVC. The tubing may extend into the interior of the container, and may be used as a siphon, for example. There may be a number of tubes providing fluid communication to any individual container, and the tubes may be oriented in a number of ways. For example, there may be at least two tubes oriented at the top of the collection bag, or at the bottom of the bag, or a tube at each end of the bag.

Additionally, the tubes, assemblies, porous media, and containers, may be oriented to define different flow paths. For example, when bone marrow is processed, a first portion may flow along a first flow path, e.g., through a 850 micron filter and into a satellite bag (e.g., a second container). Similarly, a second portion may flow along a second flow path, e.g., through a 200 micron filter assembly, and into a satellite bag (e.g., a third container). Since independent flow paths may be present, biological fluids may flow concurrently, or sequentially.

A seal, valve, clamp, transfer leg closure, or the like is typically located in or on the tubing. It is intended that the present invention is not limited by the type of material used to construct the containers or the conduit which connects the containers.

As noted above, the bone marrow is passed through one or more porous media adapted to remove one or more predetermined constituents in the bone marrow. As used herein, adapted to remove refers to a physical, biological, chemical, or other arrangement or surface enhancement intended to effect the removal of the component. For example, it may be desirable to remove all components in the bone marrow having a size greater than about 850 microns. In this embodiment, the porous media would be adapted to remove particles greater than about 850 microns by having a pore rating of about 850 microns. In a second example, it may be desirable to remove leukocytes from the bone marrow. In this embodiment, the porous media might be adapted to remove leukocytes by coating the surface of a fibrous porous media with one or more elements that attract and/or bind leukocytes. In a third example, it may be desirable to specifically remove stem cells from the bone marrow. In this embodiment, the porous media might be adapted to remove stem cells by coating the surface of a fibrous porous medium with an antibody or the like that specifically binds stem cells. It is intended that the present invention should be limited to a specific configuration of the porous medium.

The porous medium may be formed from any natural or synthetic fiber (or from other materials of similar surface area and pore size) compatible with blood. The porous medium may remain untreated. Preferably, the critical wetting surface tension (CWST) of the porous medium is within a certain range as dictated by its intended use and/or by the type of biological fluid passing through the porous medium. The pore surfaces of the medium may be modified or treated in order to achieve a desired property. Although the filter medium may remain untreated, the fibers or membrane are preferably treated to make them even more effective for separating one component from other components of bone marrow. The porous medium is preferably treated in order to reduce or eliminate platelet adherence to the medium. Any treatment which reduces or eliminates platelet adhesion is included within the scope of the present invention. Furthermore, the medium may be surface modified as disclosed in U.S. Pat. No. 4,880,548, incorporated herein by reference, in order to increase the critical wetting surface tension (CWST) of the medium and to be less adherent of platelets.

In the embodiments of the invention in which the porous medium includes fibers, the surface characteristics of the fiber may remain unmodified, or can be modified by a number of methods, for example, by chemical reaction including wet or dry oxidation; by coating the surface by depositing a polymer thereon; or by grafting reactions wherein the substrate or fiber surface is activated prior to or during wetting of the fiber surface by a monomer solution by exposure to an energy source such as heat, a Van der Graff generator, ultraviolet light, or to various other forms of radiation; or by subjecting the fibers to gas plasma treatment. A preferred method is a grafting reaction using gamma-radiation, for example, from a cobalt source.

An exemplary radiation grafting technique employs at least one of a variety of monomers each comprising an ethylene or acrylic moiety and a second group, which is preferred to be a hydrophilic group (e.g., —COOH, or —OH). Grafting of the fibrous medium may also be accomplished by compounds containing an ethylenically unsaturated group, such as an acrylic moiety, combined with a hydroxyl group, preferably monomers such as hydroxyethyl methacrylate (HEMA), or acrylic acid. The compounds containing an ethylenically unsaturated group may be combined with a second monomer such as methyl acrylate (MA), methyl methacrylate (MMA), or methacrylic acid (MAA). Analogues with similar functional characteristics may also be used to modify the surface characteristics of fibers.

If desired, the flow rate of biological fluid through the filter can be regulated to obtain a total flow period of about 10 to 40 minutes by selecting the appropriate element diameter, element thickness, fiber diameter, and density, and/or by varying the diameter of the tube either upstream or downstream of the filter, or both up and downstream.

All of these parameters can be varied; for example, the diameter of the porous medium could be reduced and the thickness increased while retaining the same total quantity of fiber, or the fibers could be larger in diameter while increasing the total quantity of fiber, or the fibers could be packed as opposed to preformed into a cylindrical disc. Such variations fall within the purview of this invention.

As noted above, as the bone marrow is expressed from the collection bag, it may be processed through a device having a leucocyte depletion element in order to reduce the leucocyte content of the bone marrow. In accordance with the invention, the porous medium for removing leucocytes from the bone marrow may comprise a leucocyte removal element or porous medium having an average diameter of from about 1 to about 4 $\mu$m, preferably from about 2 to about 3 $\mu$m. Polybutylene terephthalate (PBT) web, which is a preferred material, may be hot compressed to a voids volume of about 65% to about 90% and preferably to about 73% to about 88.5%.

The biological fluid may be supplied in any suitable quantity consistent with the capacity of the overall device and by any suitable means, e.g., in a batch operation by, for example, a collection bag connected to an expresser or a syringe, or in a continuous operation as part of, for example, an apheresis system. A source of biological fluid may also include an apheresis system, and/or may include a system in which biological fluid is re-circulated through the system.

Further, a bone marrow system according to the invention may include an access port 12 configured as or in fluid communication with a manifold valve, said manifold valve having one or more ports adapted for communicating with a syringe. In this embodiment of the invention, bone marrow may be harvested by multiple technicians using multiple syringes, and the bone marrow in multiple syringes may be transferred to the collection bag simultaneously or consecutively.

The present inventive device may similarly be part of an apheresis system. The biological fluid to be processed may be handled in either a batch or continuous manner. The sizes, nature, and configuration of the present inventive device can be adjusted to vary the capacity of the device to suit its intended environment.

Under certain circumstances, it may be desirable to maximize the recovery of a biological fluid retained or entrapped in various elements of the biological fluid processing system. For example, under typical conditions, using a typical device, the biological fluid will drain through the system until the flow is stopped, leaving some of the fluid in the system. In one embodiment of the invention, the retained fluid may be recovered by using at least one gas inlet and/or at least one gas outlet.

The invention may also comprise at least one gas inlet, and/or at least one gas outlet. For example, first container 11 may also be in fluid communication with a gas inlet, a microaggregate filter assembly 15, and a gas outlet. The assembly may also include additional containers, flow paths, and porous media. The gas outlet is a porous medium which allows gas that may be present in a biological fluid processing system when the biological fluid is processed in the system, out of the system. The gas inlet is a porous medium which allows gas into a biological fluid processing system.

As used herein, gas refers to any gaseous fluid, such as air, sterilized air, oxygen, carbon dioxide, and the like; it is intended that the invention is not to be limited to the type of gas used.

The gas inlet and gas outlet are chosen so that the sterility of the system is not compromised. The gas inlet and the gas outlet are particularly suited for use in closed systems, or may be used later, for example, within about 24 hours of a system being opened.

The gas inlet and the gas outlet each comprise at least one porous medium designed to allow gas to pass therethrough. A variety of materials may be used, provided the requisite properties of the particular porous medium are achieved. These include the necessary strength to handle the differential pressures encountered in use and the ability to provide the desired filtration capability while providing the desired permeability without the application of excessive pressure. In a sterile system, the porous medium should also preferably have a pore rating of about 0.2 micrometer or less to preclude bacteria passage.

The gas inlet and gas outlet may comprise a porous medium, for example, a porous fibrous medium, such as a depth filter, or a porous membrane or sheet. Multilayered porous media may be used, for example, a multilayered microporous membrane with one layer being liquophobic and the other liquophilic. Particularly preferred are skinless, substantially alcohol-insoluble, hydrophilic polyamide membranes, such as those described in U.S. Pat. No. 4,340,479.

The rate of air flow through the gas outlet or the gas inlet can be tailored to the specific biological fluid or fluids of interest. The rate of air flow varies directly with the area of the porous medium and the applied pressure. Generally, the area of the porous medium is designed to enable the biological fluid processing system to be primed in a required time under the conditions of use. For example, in medical applications it is desirable to be able to prime an intravenous set in from about 30 to about 60 seconds. In such applications as well as in other medical applications, the typical porous medium is a membrane, which may be in the form of a disc which has a diameter from about 1 mm to about 100 mm, preferably from about 2 mm to about 80 mm, and more preferably from about 3 mm to about 25 mm.

In accordance with the invention, the processing system may be provided with a gas inlet to permit the introduction of gas into the system, and/or with a gas outlet to permit gases in the various elements of the system to be separated from the biological fluid to be processed. The gas inlet and the gas outlet may be used together in connection with at least one assembly, porous medium, or container in the system, or they may be used separately.

To that end, a gas inlet or gas outlet may be included in any of the various elements of the biological fluid processing system. By way of illustration, a gas inlet or gas outlet may be included in at least one of the conduits which connect the different containers, in a wall of the containers that receive the processed biological fluid, or in a port on or in one of those containers. The gas inlet or gas outlet may also be included on or in a combination of the elements mentioned above. Also, an assembly or porous medium may include one or more gas inlet or gas outlet as described above. Generally, however, it is preferred to include a gas inlet or gas outlet in the conduits which connect the containers or in the functional medical device. Included within the scope of the invention is the use of more than one gas inlet or gas outlet in any conduit, receiving container, assembly, or porous medium.

It will be apparent to one skilled in the art that the placement of a gas inlet or a gas outlet may be optimized to achieve a desired result. For example, it may be desirable to locate the gas inlet upstream of a porous medium and in or as close to the first container as is practical in order to maximize the recovery of biological fluid. Also, it may be desirable to locate the gas outlet downstream of the porous medium and as close to the receiving container as is possible in order to maximize the volume of gas that is removed from the system.

Such placement of the gas inlet or gas outlet is particularly desirable where there is only one gas inlet or gas outlet in the system.

In accordance with the invention, recovery from the various elements of the biological fluid processing system may be maximized. For example, bone marrow is subjected to a processing step, resulting in filtered bone marrow. Blood product that has become entrapped in these elements during processing may be recovered either by passing purge gas through the conduits and porous media, or by creating at least a partial vacuum in the system to draw out the retained blood product and to permit it to drain into the appropriate receiving container or assembly.

The purge gas may be from any of a number of sources. For example, the biological fluid processing system may be provided with a storage container for the storage of the purge gas, the purge gas may be the gas that was removed from the system during the processing function, or the purge gas may be injected aseptically into the system from an outside source (e.g., through a syringe). For example, it may be desirable to use sterile purge gas that has been sterilized in a separate container apart from the biological fluid processing system.

In accordance with the invention, a clamp, closure, or the like may be positioned on or in any or all of the conduits in order to facilitate a desired function, i.e., establishing a desired flow path for biological fluid or gas.

The gases separated by the gas outlet may be vented from the system, or they may be collected in a gas container (not shown) and returned to the system as a purge gas to facilitate the recovery of biological fluid that becomes trapped in the various components of the system.

After the system is primed and the gas outlet is inactivated, the clamp adjacent to the containers or assembly is opened to allow the containers to fill with processed biological fluid. This continues until the collection bag 11 collapses. In order to recover the very valuable biological fluid retained in the system, ambient air or a sterile gas may enter the system through gas inlet. If gas inlet is a manual inlet means, a closure is opened or a clamp released; if the gas inlet is automatic, the pressure differential between the gas inlet and the containers will cause the air or gas to flow through the conduits, through the porous media, and towards the respective containers. In the process, retained biological fluid that is trapped in those elements during processing are recovered from those components and collected in the containers. It should be noted that the purge air or gas is preferably separated from the biological fluid at gas outlet so that little, if any, purge gas will be received by the containers. This may be accomplished by clamping the conduit downstream of the gas outlet. In another embodiment of the invention, the purge air or gas may be separated from the system through a gas outlet located in the bag itself.

A system according to the present invention may be used in conjunction with other assemblies or porous media, including filtration and/or separation devices, e.g., a device for removing leucocytes from a platelet-containing solution or concentrate.

A number of additional containers may be in communication with the biological fluid processing system, and can be utilized to define different flow paths. For example, an additional satellite bag containing physiological solution may be placed in communication with the biological fluid processing system upstream of the filter assembly, and the solution may be passed through the filter assembly so that the biological fluid that was held up in the assembly can be collected.

It will be appreciated that when the biological fluid from the collection bag 11 is expressed towards the containers, some of the biological fluid may be trapped in the conduits and/or the porous mediums. For example, 8 cc to 35 cc is typically retained in the system; but as little as 2 cc to as much as 150 cc or more may be retained in some types of systems.

In an embodiment of the invention (not shown), air or gas may be stored in at least one gas container; upon opening of valve or clamp means in the conduits, gas can be fed through them to purge the conduits and assemblies, thereby facilitating the recovery of biological fluid that may have been trapped during processing.

Preferably, the purge air or gas is fed to the conduits at a point as close as is reasonably possible to container 11 to maximize the volume of biological fluid recovered. The air or gas container is preferably flexible so that the gas therein may be fed to the system merely by simple compression. The biological fluid containers and the air or gas containers may be composed of the same material.

In an embodiment of the invention (not shown), priming fluid may be stored in at least one container; upon opening of valve or clamp means in the conduits, priming fluid can be fed through them to prime and/or wet the conduits and assemblies, thereby facilitating the function and operation of the various elements in the system. Priming fluid includes but is not limited to a solution or composition containing bone marrow, an anti-coagulant solution, or any solution compatible with bone marrow and effective as a wetting or priming solution.

It will be apparent to one skilled in the art that the placement and connection of a source of priming fluid to the system may be optimized to achieve a desired result.

Priming, as used herein, refers to wetting or priming the inner surfaces of a device or assembly prior to its actual use allowing a separate assembly to be injected into the system. A valve or clamp is opened to allow fluid to flow through the assembly; then, with the passage of fluid through the assembly, gas downstream of the fluid is expelled through the gas outlet until fluid reaches a branching element, at which point the clamp is closed. With the clamp in a closed position, the connector downstream of the gas outlet may be opened or readied for use without fluid in the assembly dripping through the connector.

In accordance with the invention, the biological fluid collection and processing assembly should be able to withstand rigorous sterilization, typically consisting of radiation sterilization (at about 2.5 megarads), and/or autoclaving (at about 110° C. to about 120° C. for about 15 to 60 minutes).

There may be a clamp or the like between the collection bag 11 and the flexible tubing or within the tubing, to prevent the flow of the bone marrow from entering the wrong conduit.

Movement of the biological fluid through the system is effected by maintaining a pressure differential between the source of the biological fluid and the destination of the biological fluid (e.g., a container such as a satellite bag or a needle on the end of a conduit). The system of the invention is suitable for use with conventional devices for establishing the pressure differential, e.g., an expresser. Exemplary means of establishing this pressure differential may be by gravity head, applying pressure to the collection bag (e.g., by hand or with a pressure cuff), or by placing the other container (e.g., satellite bag) in a chamber (e.g., a vacuum chamber) which establishes a pressure differential between the collection bag and the other container. Also included within the scope of the invention may be expressors which generate substantially equal pressure over the entire collection bag.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

What is claimed is:

1. A method for collecting and processing bone marrow comprising transferring harvested bone marrow into a sealed first container by passing the harvested bone marrow through at least one manifold; processing the harvested bone marrow; passing the processed bone marrow into a second container; passing a solution housed in a third container through the manifold; and then returning the solution to the third container.

2. The method of claim 1 further comprising passing the solution in the third container into the first container.

* * * * *